US 8,092,533 B2

(12) United States Patent
Melkent

(10) Patent No.: US 8,092,533 B2
(45) Date of Patent: Jan. 10, 2012

(54) DYNAMIC DEVICES AND METHODS FOR STABILIZING VERTEBRAL MEMBERS

(75) Inventor: Anthony J. Melkent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 383 days.

(21) Appl. No.: 11/538,180

(22) Filed: Oct. 3, 2006

(65) Prior Publication Data

US 2008/0161919 A1 Jul. 3, 2008

(51) Int. Cl.
*A61F 2/44* (2006.01)

(52) U.S. Cl. ................... 623/17.11; 623/17.16

(58) Field of Classification Search ............ 606/60, 606/248–249, 279; 623/17.11–17.16
See application file for complete search history.

(56) References Cited

U.S. PATENT DOCUMENTS

| | | | |
|---|---|---|---|
| 4,997,432 A | 3/1991 | Keller | |
| 5,192,327 A | 3/1993 | Brantigan | |
| 5,320,644 A * | 6/1994 | Baumgartner | 623/17.16 |
| 5,423,817 A | 6/1995 | Lin | |
| 5,609,637 A | 3/1997 | Biedermann et al. | |
| 5,645,599 A * | 7/1997 | Samani | 623/17.16 |
| 5,672,175 A | 9/1997 | Martin | |
| 5,676,702 A | 10/1997 | Ratron | |
| 5,749,916 A | 5/1998 | Richelsoph | |
| 5,984,967 A | 11/1999 | Zdblick et al. | |
| 6,106,557 A | 8/2000 | Robioneck et al. | |
| 6,136,031 A * | 10/2000 | Middleton | 623/17.16 |
| 6,143,031 A | 11/2000 | Knothe et al. | |
| 6,149,652 A | 11/2000 | Zucherman et al. | |
| 6,159,211 A | 12/2000 | Boriani et al. | |
| 6,238,397 B1 | 5/2001 | Zucherman et al. | |
| 6,280,444 B1 | 8/2001 | Zucherman et al. | |
| 6,296,664 B1 * | 10/2001 | Middleton | 623/17.15 |
| 6,379,355 B1 | 4/2002 | Zucherman et al. | |
| 6,395,035 B2 * | 5/2002 | Bresina et al. | 623/17.15 |
| 6,402,750 B1 | 6/2002 | Atkinson et al. | |
| 6,432,106 B1 | 8/2002 | Fraser | |
| 6,440,169 B1 * | 8/2002 | Elberg et al. | 623/17.16 |
| 6,447,548 B1 | 9/2002 | Ralph et al. | |
| 6,451,020 B1 | 9/2002 | Zucherman et al. | |
| 6,468,311 B2 | 10/2002 | Boyd et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,554,863 B2 | 4/2003 | Paul et al. | |
| 6,562,074 B2 | 5/2003 | Gerbec et al. | |
| 6,579,321 B1 * | 6/2003 | Gordon et al. | 623/17.16 |

(Continued)

OTHER PUBLICATIONS

Melkent, Anthony J., "Dynamizing Interbody Implant and Methods for Stabilizing Vertebral Members." Filed on Oct. 3, 2006, 24 pages, U.S. Appl. No. 11/538,190.

*Primary Examiner* — Thomas C. Barrett
*Assistant Examiner* — Matthew Lawson

(57) ABSTRACT

Implants and methods for dynamic stabilization and/or fusion of vertebral members. The implant includes relief cuts that provide flexibility to accommodate relative movements of the vertebral members. The number, size, and shape of the relief cuts may vary depending upon the desired flexibility. Shims are sized to fit within the relief cuts to adjust the flexibility of the implant. The shims may be placed within the relief cuts to adjust the overall flexibility of the implant. In general, the stiffness of the device increases with an increase in the number of shims. Shims may also be placed within specific relief cuts to adjust the flexibility for predetermined vertebral movement.

19 Claims, 7 Drawing Sheets

U.S. PATENT DOCUMENTS

| | | |
|---|---|---|
| 6,582,433 B2 | 6/2003 | Yun |
| 6,626,944 B1 * | 9/2003 | Taylor .................. 623/17.16 |
| 6,648,917 B2 | 11/2003 | Gerbec et al. |
| 6,682,564 B1 | 1/2004 | Duarte |
| 6,719,794 B2 | 4/2004 | Gerber et al. |
| 6,719,795 B1 | 4/2004 | Cornwall et al. |
| 6,796,983 B1 | 9/2004 | Zucherman et al. |
| 6,830,589 B2 | 12/2004 | Erickson |
| 6,846,328 B2 | 1/2005 | Cauthen |
| 6,869,445 B1 | 3/2005 | Johnson |
| 6,893,464 B2 | 5/2005 | Kiester |
| 6,893,466 B2 * | 5/2005 | Trieu .................. 623/17.16 |
| 6,964,686 B2 * | 11/2005 | Gordon .................. 623/17.14 |
| 7,041,135 B2 * | 5/2006 | Michelson ............ 623/17.11 |
| 7,238,204 B2 * | 7/2007 | Le Couedic et al. ....... 623/17.11 |
| 2001/0007073 A1 | 7/2001 | Zucherman et al. |
| 2001/0016743 A1 | 8/2001 | Zucherman et al. |
| 2001/0021850 A1 | 9/2001 | Zucherman et al. |
| 2001/0031965 A1 | 10/2001 | Zucherman et al. |
| 2002/0143329 A1 * | 10/2002 | Serhan et al. .................. 606/61 |
| 2003/0095154 A1 | 5/2003 | Tuomi et al. |
| 2003/0191470 A1 | 10/2003 | Ritland |
| 2004/0049190 A1 | 3/2004 | Biedermann et al. |
| 2004/0122518 A1 * | 6/2004 | Rhoda .................. 623/17.11 |
| 2004/0133279 A1 * | 7/2004 | Krueger et al. ........... 623/17.16 |
| 2004/0153156 A1 | 8/2004 | Cohen et al. |
| 2004/0220568 A1 | 11/2004 | Zucherman et al. |
| 2004/0236328 A1 | 11/2004 | Paul et al. |
| 2005/0049708 A1 | 3/2005 | Atkinson et al. |
| 2005/0085812 A1 | 4/2005 | Sherman et al. |
| 2005/0085814 A1 | 4/2005 | Sherman et al. |
| 2005/0101955 A1 | 5/2005 | Zucherman et al. |
| 2005/0143738 A1 | 6/2005 | Zucherman et al. |
| 2005/0165398 A1 | 7/2005 | Reiley |
| 2005/0192574 A1 | 9/2005 | Blain |
| 2005/0196420 A1 | 9/2005 | Zucherman et al. |
| 2005/0203512 A1 * | 9/2005 | Hawkins et al. ................. 606/61 |
| 2005/0209603 A1 | 9/2005 | Zucherman et al. |
| 2005/0228383 A1 | 10/2005 | Zucherman et al. |
| 2005/0228384 A1 | 10/2005 | Zucherman et al. |
| 2005/0288672 A1 | 12/2005 | Ferree |
| 2006/0009768 A1 | 1/2006 | Ritland |
| 2006/0015184 A1 * | 1/2006 | Winterbottom et al. ... 623/18.11 |
| 2006/0047341 A1 * | 3/2006 | Trieu .................. 623/17.12 |
| 2007/0167945 A1 * | 7/2007 | Lange et al. .................. 606/61 |
| 2007/0191837 A1 * | 8/2007 | Trieu .................. 606/61 |
| 2007/0191838 A1 * | 8/2007 | Bruneau et al. .................. 606/61 |
| 2007/0191946 A1 * | 8/2007 | Heinz et al. ................ 623/17.11 |
| 2007/0191953 A1 * | 8/2007 | Trieu .................. 623/17.15 |
| 2007/0225810 A1 * | 9/2007 | Colleran et al. ........... 623/17.13 |
| 2007/0233096 A1 * | 10/2007 | Garcia-Bengochea ......... 606/61 |
| 2007/0239278 A1 * | 10/2007 | Heinz .................. 623/17.15 |
| 2007/0260324 A1 * | 11/2007 | Joshi et al. .................. 623/23.51 |
| 2007/0270957 A1 * | 11/2007 | Heinz .................. 623/17.11 |
| 2008/0015692 A1 * | 1/2008 | Heinz .................. 623/17.11 |
| 2008/0161920 A1 * | 7/2008 | Melkent .................. 623/17.11 |
| 2008/0306609 A1 * | 12/2008 | Lee et al. .................. 623/23.58 |

* cited by examiner

DYNAMIC DEVICES AND METHODS FOR STABILIZING VERTEBRAL MEMBERS

BACKGROUND

The present application is directed to implants and methods for dynamic stabilization and/or fusion of vertebral members and, more specifically, to implants and methods of inserting one or more shims within relief cuts in the body of the implant to selectively adjust the stiffness.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Implants may be positioned between the vertebral members to stabilize the spine. The implants may also replace an entirety or a section of a vertebral member, the entirety or a section of an intervertebral disc, or both. Implants may also provide support and stabilization without removing the damaged vertebral members or discs. The implants should reduce or eliminate the pain and neurological deficit.

SUMMARY

The present application is directed to implants and methods for dynamic stabilization and/or fusion of vertebral members. The implants include a body with relief cuts that provide flexibility to accommodate relative movements of the vertebral members. The number, size, and shape of the relief cuts may vary depending upon the desired flexibility. Shims are sized to fit within the relief cuts to adjust the flexibility of the implant. In general, the stiffness of the device increases with an increase in the number of shims. Shims may also be placed within specific relief cuts to adjust the flexibility for stabilization of specific vertebral movements.

DETAILED DESCRIPTION

The present application is directed to implants and methods for dynamic stabilization and/or fusion of vertebral members. The implants include relief cuts that provide flexibility to accommodate relative movements of the vertebral members. The number, size, and shape of the relief cuts may vary depending upon the desired flexibility. Shims are sized to fit within the relief cuts to adjust the flexibility of the implant. The shims may be placed within specific relief cuts to adjust the overall flexibility of the implant. Shims may also be placed within specific relief cuts to adjust the flexibility for specific vertebral movements.

Figure 1:
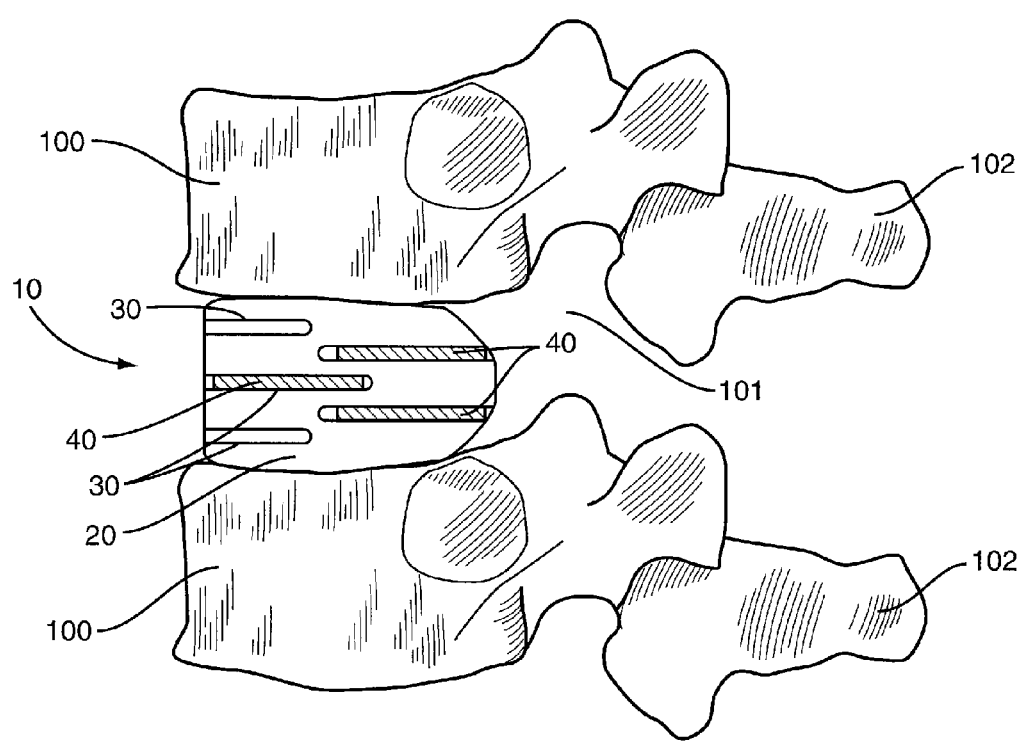
FIG. 1 is a side view of an implant positioned between vertebral members according to one embodiment.
Figure 2:
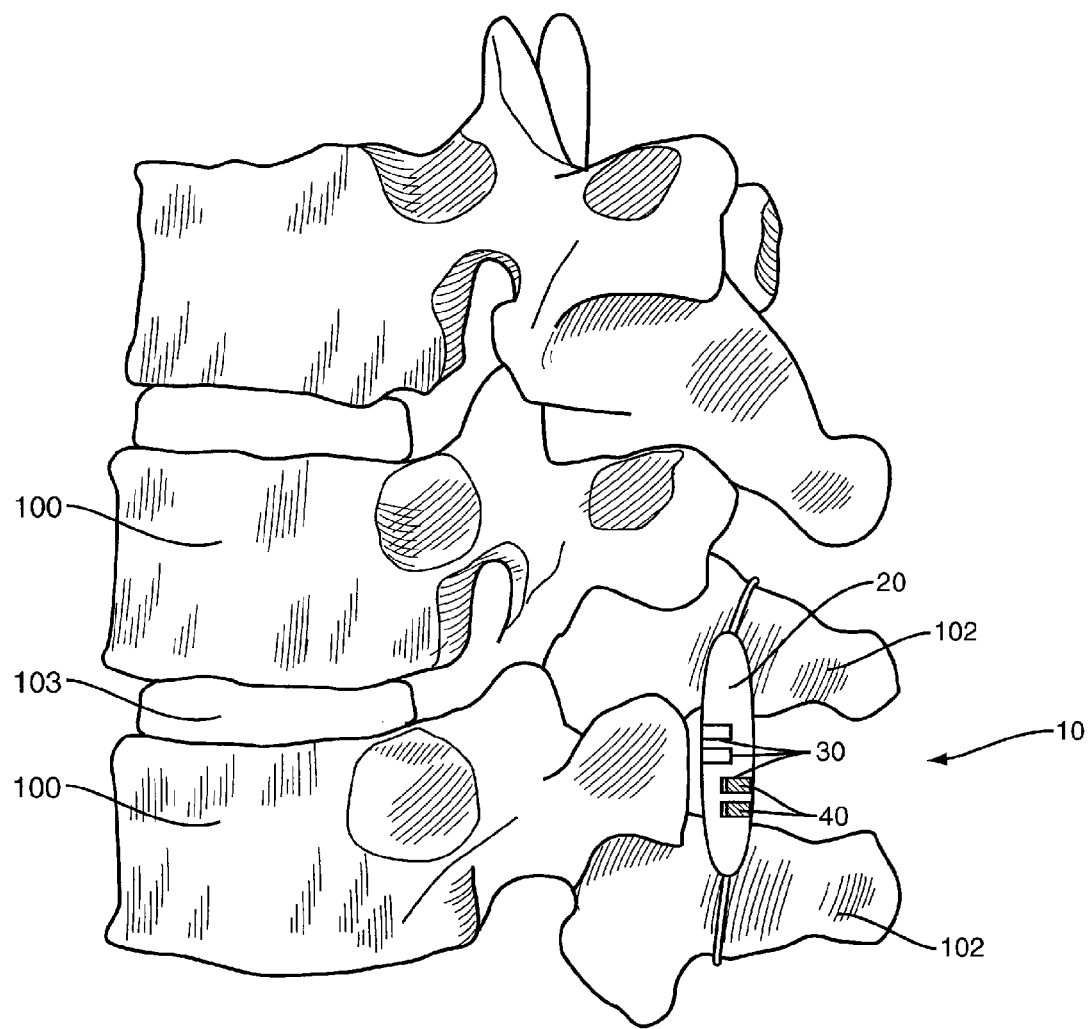
FIG. 2 is a side view of an implant positioned between vertebral members according to one embodiment.

FIGS. 1 and 2 illustrate embodiments of implants 10. FIG. 1 includes the implant 10 positioned within the intervertebral space 101 formed between vertebral members 100. FIG. 2 includes an interspinous implant 10 positioned between the spinous processes 102. The implants 10 include a body 20 sized to fit within the desired space. Relief cuts 30 are formed within the body 20. The size, shape, and number and relief cuts 30 may vary depending upon the context of use. Shims 40 are sized to fit within the relief cuts 30 to adjust the stiffness of the implant 10. The implant 10 may include a minimum stiffness when no shims 40 are inserted within the cuts 30. Maximum stiffness may occur when shims 40 are inserted within each cut 30. Shims 40 may also be positioned within specific areas of the body 20 to selectively adjust the stiffness for a particular vertebral motion. In one embodiment, shims 40 are inserted in the anterior cuts 30 of an intervertebral implant 10 to increase the stiffness against flexion.

Figure 3:
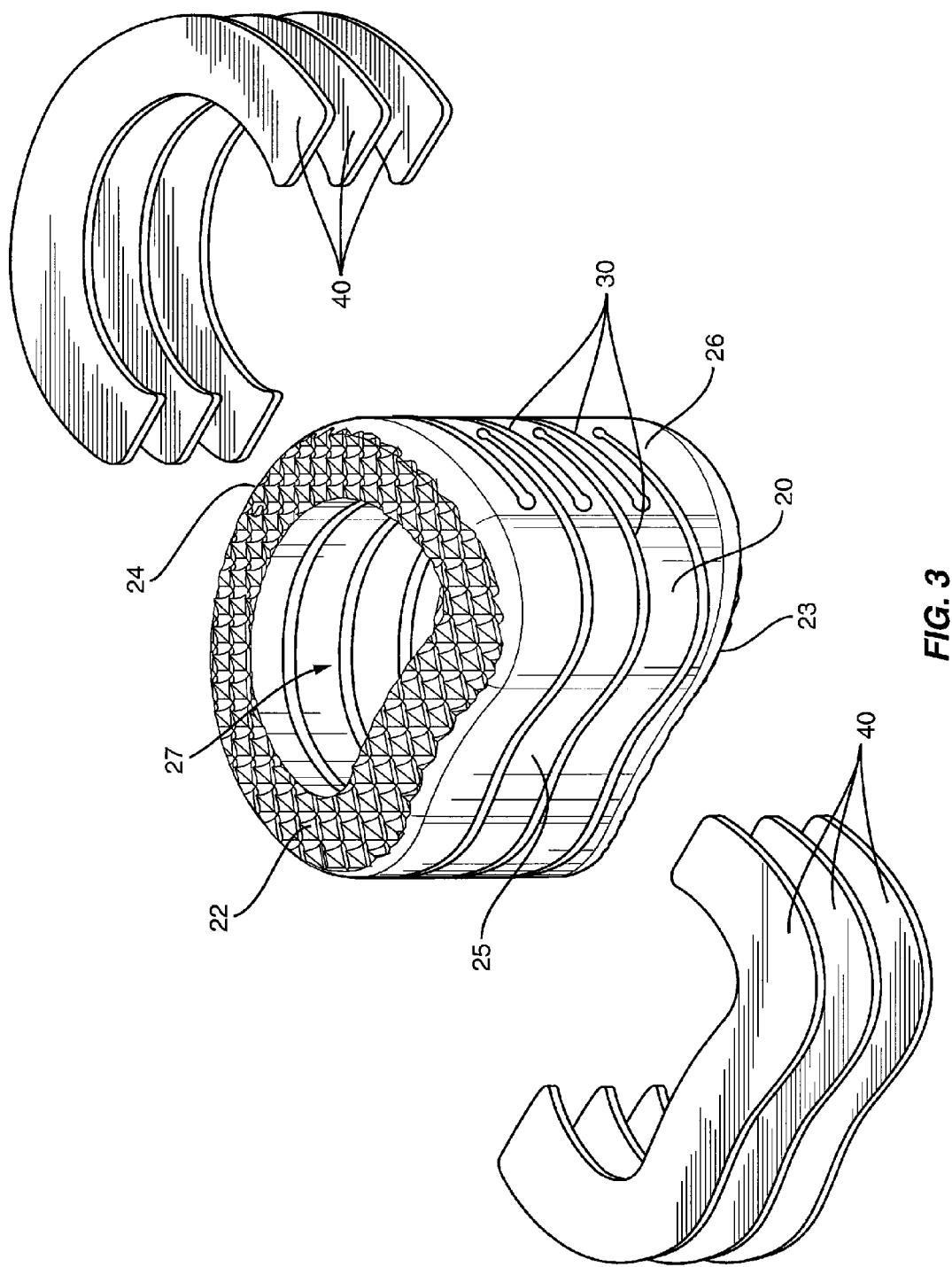
FIG. 3 is an exploded perspective view of an implant comprising a body and shims according to one embodiment.
Figure 4:
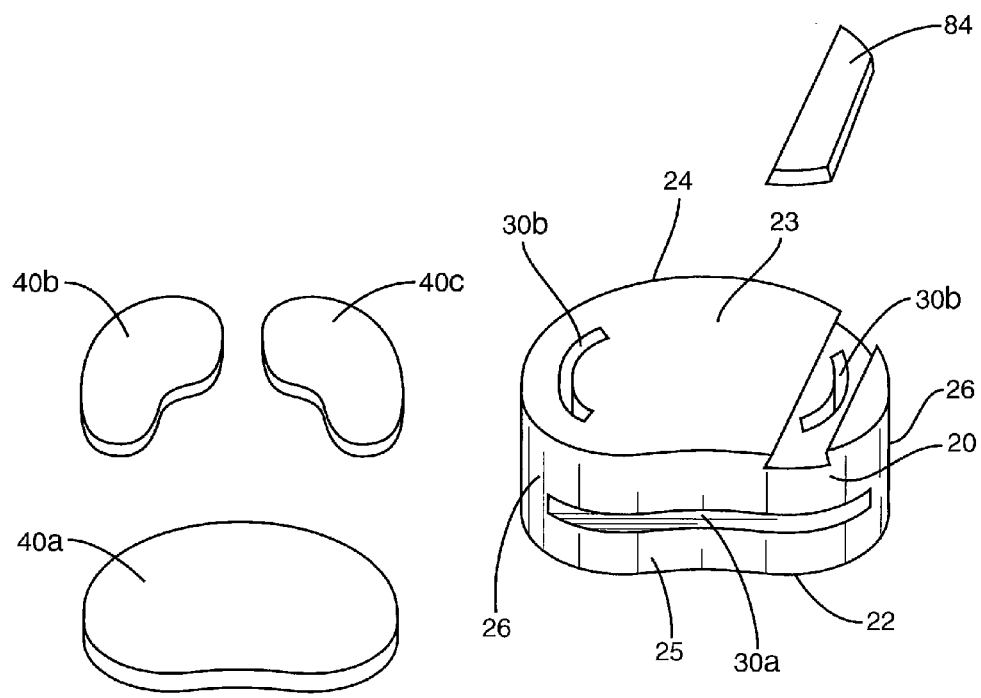
FIG. 4 is a perspective view of a body and a variety of shims according to one embodiment.
Figure 5:
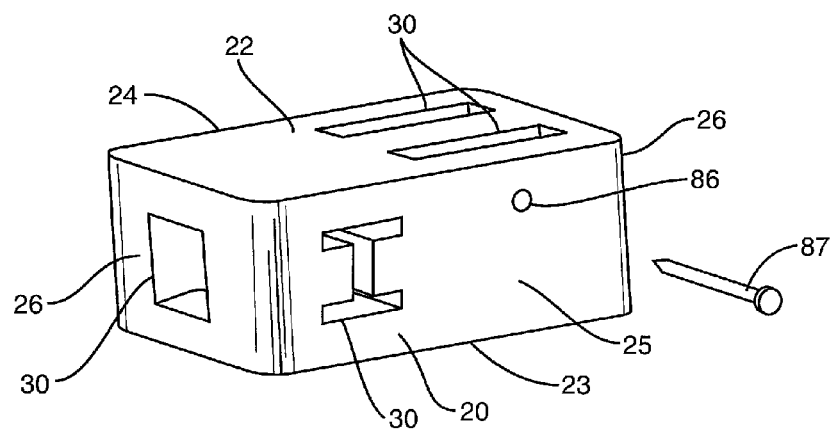
FIG. 5 is a perspective view of an implant according to one embodiment.

FIG. 3 illustrates an exploded view of one embodiment of the implant 10 that comprises a body 20 and shims 40. The body 20 is sized for positioning within the intervertebral space 101. Body 20 includes a superior side 22 and inferior side 23 that each contacts one of the vertebral members 100. These sides 22, 23 may include teeth for engaging the vertebral members 100. Body 20 further includes an anterior side 24, posterior side 25, and lateral sides 26. Other embodiments of the body 20 may include a variety of shapes and sizes. In one embodiment, the body 20 is substantially cylindrical with curved sides. FIG. 4 illustrates an embodiment with a body 20 that does not include an aperture 27. The body 20 may be solid, or may include a hollow interior. FIG. 5 includes another embodiment of a body 20 with a substantially rectangular shape.

Figure 6:
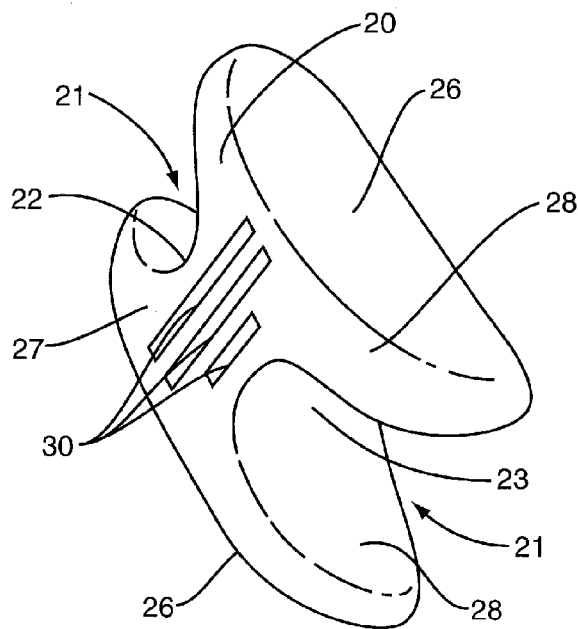
FIG. 6 is a perspective view of an implant according to one embodiment.
Figure 7:
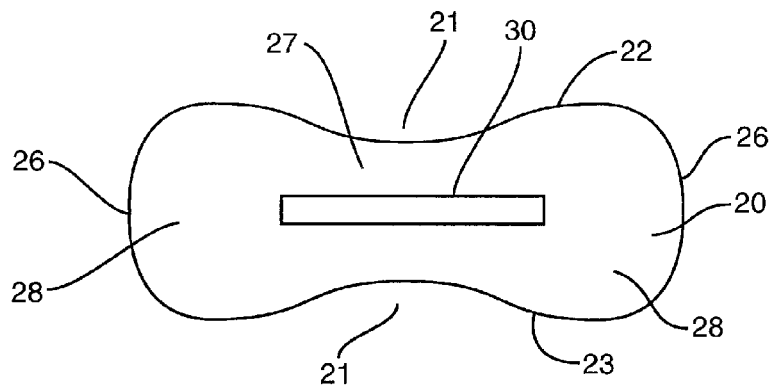
FIG. 7 is a side view of an implant according to one embodiment.
Figure 8:
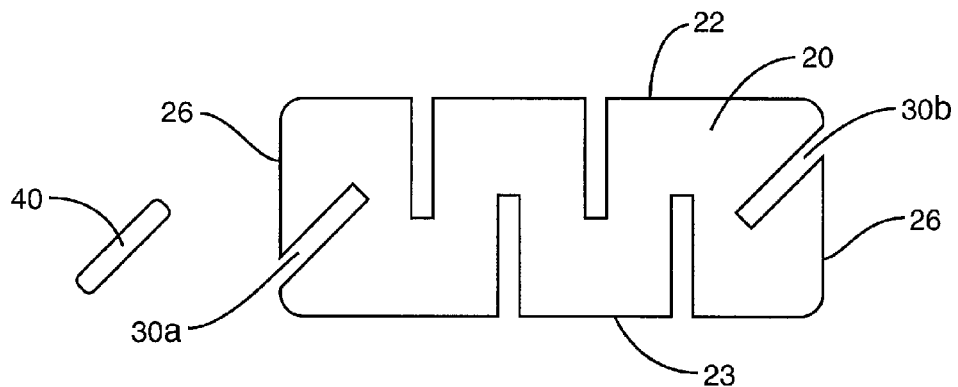
FIG. 8 is a side view of an implant according to one embodiment.

FIG. 6 illustrates an embodiment for spacing apart the spinous processes 102. This body 20 includes a core 27 with a pair of lateral wings 28 that together form channels 21 for receiving the spinous processes 102. FIG. 7 illustrates another embodiment of an interspinous body with less pronounced channels 21 formed by the core 27 and wings 28. FIG. 8 includes another embodiment of a body 20 that may be used for insertion in either the interspinous or intervertebral spaces.

Figure 9:
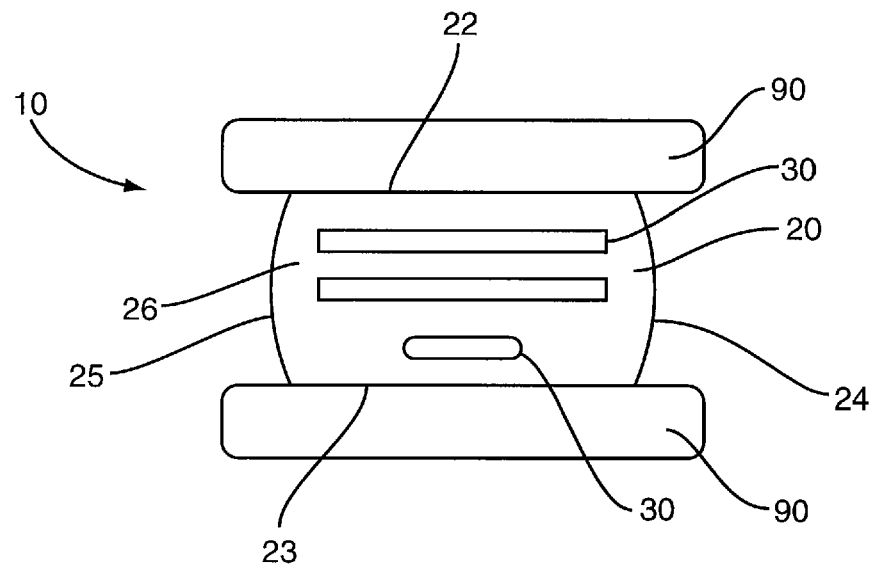
FIG. 9 is a side view of an implant according to one embodiment.

Body 20 may further be positioned between one or more mounts 90. FIG. 9 includes an intervertebral implant 10 with a body 20 positioned between opposing mounts 90. Mounts 90 are sized and shaped to contact the vertebral members 100 and position the body 20 within the intervertebral space 101. Body 20 includes superior and inferior sides that contact the mounts 90. Body 20 may include a variety of shapes and sizes. The embodiment illustrated in FIG. 9 is for use within the intervertebral space 101.

Figure 10:
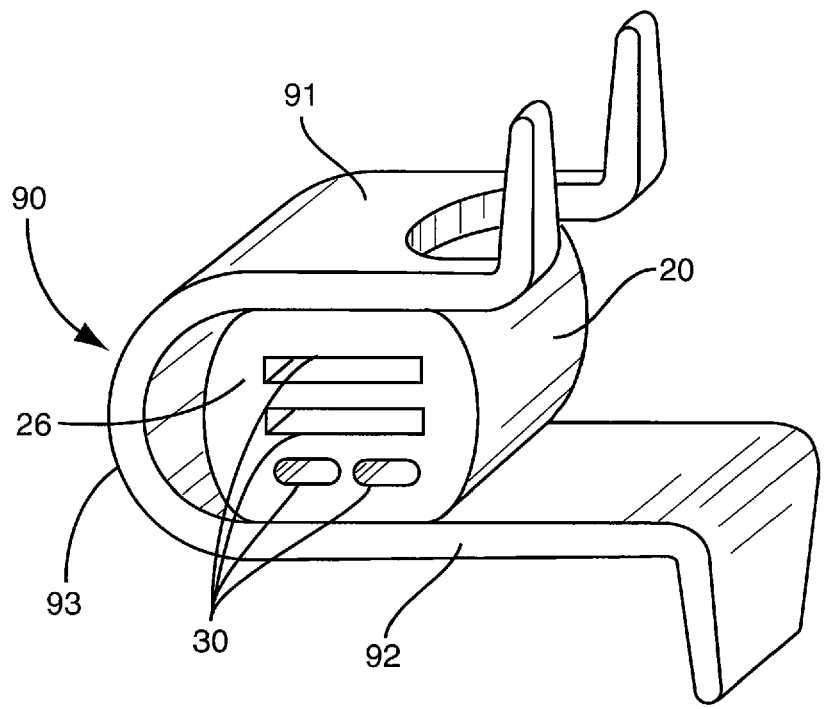
FIG. 10 is a perspective view of an implant according to one embodiment.

FIG. 10 illustrates another embodiment with a single mount 90 sized to receive the body 20. Mount 90 includes superior and inferior sections 91, 92 that contact the vertebral members 100. An intermediate section 93 extends between the sections 91, 92. Body 20 is sized to fit within the space formed by the sections 91, 92, 93. Body 20 may be connected to one or more of the sections 91, 92, 93 to maintain the position within the mount 90. This embodiment is constructed to fit within the interspinous space between the spinous processes 102.

Body 20 may be formed of a variety of materials. Embodiments feature materials such as metals suitable for surgical implants such as stainless steel, titanium, nickel titanium, and cobalt chromium. Body 20 may also be formed of bone. Polymer materials may also be used, including members of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Body 20 may also be constructed of a substantially elastic material such as elastomeric materials, hydrogels or other hydrophilic-polymers, or composites thereof. Suitable elastomers include silicone, polyurethane, copolymers of silicone and polyurethane, polyolefins, such as polyisobutylene and polyisoprene, neoprene, nitrile, vulcanized rubber and combinations thereof. Suitable hydrogels include natural hydrogels, and those formed from polyvinyl alcohol, acrylamides such as polyacrylic acid and poly(acrylonitrile-acrylic acid), polyurethanes, polyethylene glycol, poly(N-vinyl-2-pyrrolidone), acrylates such as poly(2-hydroxy ethyl methacrylate) and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Other suitable hydrophilic polymers include naturally-occurring materials such as glucomannan gel, hyaluronic acid, polysaccharides, such as cross-linked carboxyl-containing polysaccharides, and combinations thereof.

The body 20 may be constructed of a single material, or two or more combinations of materials. Further, the body 20 may include a substantially solid, uniform construction, or may include internal chambers or pores for receiving bone growth promoting material.

One or more relief cuts 30 are positioned within the body 20. The term "relief cuts" is used in a general sense to indicate the spaces in the body 20 for holding one or more shims 40. Relief cuts 30 include a superior side and an inferior side. The height of the cuts 30 measured between the sides may vary. The relief cuts 30 may include a variety of shapes and sizes, and may extend into the body 20 from a variety of different directions. FIGS. 1, 2, and 3 illustrate embodiments with relief cuts 30 extending into the body 20 from the anterior side 24 and the posterior side 25. The cuts 30 are sized such that they extend around to the lateral sides 26 of the body 20. The cuts 30 may further be sized to overlap between the superior and inferior sides 22, 23. The overlapped cuts 30 may be alternating with posterior cuts spaced apart by anterior cuts as illustrated in FIGS. 1 and 3, or the posterior and anterior cuts may be grouped as illustrated in FIG. 2. The cuts 30 may be substantially parallel as illustrated in FIGS. 1, 2, and 3, or they may be non parallel. FIG. 7 illustrates an embodiment with a single cut 30.

Figure 11:
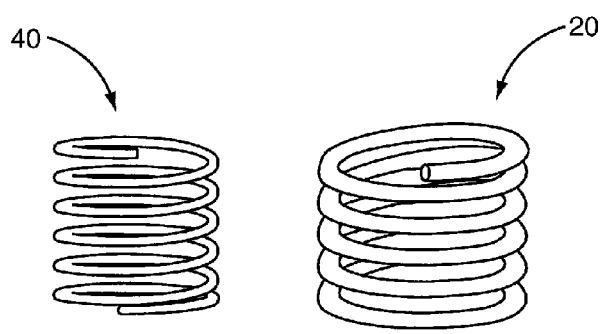
FIG. 11 is a perspective view of a shim and a body according to one embodiment.

Cuts 30 may extend into the body 20 from various sides, such as the lateral sides 26 as illustrated in FIGS. 9 and 10. Cuts 30 may also extend into the body 20 from the superior and inferior sides 22, 23 as illustrated in FIGS. 4 and 5. Cuts 30 may extend entirely through the body 20 (e.g., extend from the posterior side 25 to the anterior side 24), or they may terminate within an interior region of the body 20. Cuts 30 may further include a variety of different heights and widths sized to receive a single shim 40 or multiple shims 40. Cuts 30 may further intersect within the body 20. FIG. 4 illustrates an embodiment with cuts 30b intersecting with cut 30a. Cuts 30 may also be planar, or non-planar. FIG. 11 illustrates a cut with multiple different areas to receive a corresponding shim 40. The different areas in the body 20 extend between the coils of the shim 40.

The relief cuts 30 also decrease the stiffness of the body 20. The number, size, and shape of the cuts 30 are each factors that affect the overall stiffness of the body 20. The shape and size of the cuts 30 may also affect the amount of deflection of the body 20. By way of example, cuts 30 with greater heights may provide for greater amounts of deflection than smaller, narrower cuts 30.

Shims 40 are discrete members separate from the body 20 and sized to fit within the cuts 30 to customize the stiffness of the implant 10. The implant 10 should have an adequate stiffness to space apart the vertebral members 100, and also provide for movement such as flexion, extension, lateral bending, and rotation. Shims 40 may increase an overall stiffness of the body 20, or increase the stiffness of a particular region of the body 20 to affect one or more particular vertebral movements. The term stiffness is used to refer to the resistance of an elastic body to deflection by an applied force. In general, the body 20 has the greatest flexibility when no shims 40 are inserted within the cuts 30. The body 20 has the greatest stiffness when the maximum number of shims 40 are inserted in the cuts 30. Intermediate levels of flexibility and stiffness may be obtained by insertion of shims 40 between the maximum and minimum numbers.

Figure 12:
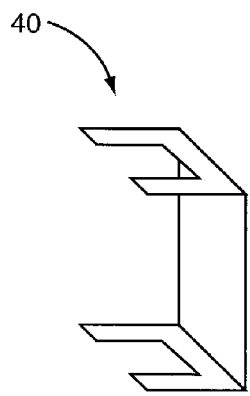
FIG. 12 is a perspective view of a shim according to one embodiment.

FIGS. 3 and 4 illustrate embodiments of shims 40. Shims 40 are discrete members that may be inserted and removed from the body 20 as necessary to adjust the stiffness. Shims 40 may include a predefined shape and size. Shims 40 include a height, width, and length to fit within the relief cuts 30. Shims 40 may be contained within the body 20 upon being fully inserted into the cuts 30. In some embodiments, shims 40 extend outward an amount from the cuts 30. In one embodiment, shims 40 are larger than the cuts 30 and therefore extend outward when fully inserted into the body 20. In other embodiments, shims 40 are smaller than the relief cuts 30. Shims 40 may be substantially planar as illustrated in FIGS. 3 and 4, or non-planar as illustrated in the coilshaped shim 40 of FIG. 11, and the shim 40 of FIG. 12.

Shims 40 may be sized such that a single shim 40 fits within each cut 30. Additionally, the shims 40 may include a width and/or height for multiple shims 40 to fit within a cut 30. In multiple shim embodiments, the shims 40 may or may not overlap. During overlap, the shims may overlap in a vertical direction with two or more shims aligned between the superior and inferior sides 22, 23, or in a horizontal direction with two or more shims aligned between lateral sides 26.

In some embodiments, shims 40 are sized to extend across a substantial area of the body 20. FIG. 4 illustrates an embodiment with a shim 40 that is substantially the same cross-sectional shape and size of the body 20. Shim 40a is sized to fit within the relief cut 30a and increase the overall stiffness of the spacer 10 and have an affect on a plurality of vertebral movements. In another embodiment, shims 40b, 40c may be inserted within cut 30a. The combination of these shims 40b, 40c causes a similar change in the stiffness of the spacer 10 as the insertion of single shim 40a.

FIG. 3 illustrates another embodiment including a plurality of shims 40 each sized to fit within a cut 30. Each shim 40 is substantially equal in size and inter-changeable to fit within each of the cuts 30. The size of the shims 40 is less than the overall cross-section of the body 20 and therefore may have an effect on the stiffness for specific movements. By way of example, the shims 40 inserted into the cuts on the anterior side 24 may increase the stiffness of the anterior of the body 20. This may cause an affect during extension and/or flexion. The curved shape of the shims 40 further extends to the lateral sides 26 that may affect lateral bending.

Shims 40 may also include a relatively small size compared to the body 20. FIG. 8 includes a shim 40 sized to fit within one of cuts 30a and 30b. The cuts 30a, 30b are positioned at the lateral sides 26 of the body 20 and insertion of the shim 40 may affect lateral bending. Insertion of shim 40 may cause little to no effect on flexion and extension movements. In one embodiment, shims 40 are sized and/or shaped to fit within less than each of the cuts 30 within the body 20. In other embodiments such as illustrated in FIG. 3, each of the shims 40 is substantially the same size and shape and are able to fit within each of the cuts 30.

Two or more shims 40 may be used in combination for adjusting the stiffness of the body 20. By way of example using the embodiment of FIG. 3, a single shim 40 inserted within an anterior cut 40 may affect a specific vertebral movement, such as flexion but not have a great affect on the overall stiffness of the body 20. However, insertion of a posterior shim 40 at a point adjacent to the anterior shim 40 may act in combination to affect the overall stiffness of the body 20.

Shims 40 may be constructed of the same types of materials as described above for the body 20. These materials may include metals, bone, and polymer materials. Shims 40 may also be elastic and constructed of elastomeric materials, hydrogels or other hydrophilic-polymers. Shims 40 may be constructed of a uniform single material, or composites of two or more of these materials.

Shims 40 may also be constructed of a resorbable material. Resorbable material may function to affect an overall stiffness of the device 10. In one embodiment, the resorbable material and the body 20 work in combination to support the vertebral members 100 when the implant 10 is initially implanted within the patient. Over time, the resorbable shim 40 is absorbed within the patient and the stiffness lessens or changes resulting in the body 20 providing an increasing amount of the support characteristics of the overall implant 10. In one embodiment, the resorbable material is completely absorbed by the body with only the body 20 and other shims 40 remaining.

In one embodiment, one or more of the shims 40 are constructed of resorbable material. During an initial period, the resorbable material shims 40 maintain their integrity and adjust the stiffness of the implant 10. The resorbable shims 40 may slowly absorb causing the overall stiffness of the implant 10 to gradually lessen. During this period, the overall stiffness properties of the implant 10 are shared by both the body 20 and shims 40. After the shim 40 of the resorbable material is completely absorbed, the body 20 and any remaining non-resorbable shims 40 provide the support characteristics of the implant 10 and control the movements of the vertebral members 100. One embodiment of an implant with a resorbable material is disclosed in U.S. patent application Ser. No. 11/538,190 filed on the same date as this application and entitled "Dynamizing Interbody Implant and Methods for Stabilizing Vertebral Members", herein incorporated by reference.

Resorbable material may be formed from a wide variety of natural or synthetic materials. The material may be elastic or elastomeric, deformable, or non-compliant. Suitable resorbable materials include fibrin, albumin, collagen, elastin, silk and other proteins, polyethylene oxide, cyanoacrylate, polylactic acid, polyester, polyglycolic acid, polypropylene fumarate, tyrosine-based polycarbonate and combinations thereof. Other suitable materials include demineralized bone matrix. In one embodiment, resorbable material may be a woven fabric.

In some embodiments, each shim 40 within the body 20 is constructed of a resorbable material. In another embodiment, the implant 10 includes multiple shims 40 with a first number being constructed of resorbable materials, and the remainder not being constructed of non-resorbable materials.

In some embodiments, one or more of the shims 40 are constructed from a different material than the body 20. Each of the multiple shims 40 may be constructed of the same material, or each of a different material. In other embodiments, one or more of the shims 40 are constructed from the same material as the body 20.

Shims 40 may be maintained within the body 20 in a variety of different manners that may include internal means or external means. In one embodiment, the shims 40 tightly fit within the cuts 30 and are maintained by an interference or friction fit. In another embodiment as illustrated in FIG. 5, an aperture 86 within the body 20 extends into one or more cuts 30. The aperture 86 is sized to receive a fastener 87 such as a screw, pin, rivet, and the like, to contact and maintain the shim 40 within the cut 30. In another embodiment, fastener 87 is inserted adjacent to the cut 30 with the head of the fastener 87 extending over the cut 30 to contain the shim 40. In another embodiment as illustrated in FIG. 4, a cover 84 is sized to extend over the cut 30 and contain the shim 40. Snap fit mechanisms may also be used that include barbs or ball-and-detent configurations to maintain the shims 40.

The implant 10 may be used in a variety of manners. The shims 40 may be positioned within the cuts 30 before or after the body 20 is inserted within the patient. In one embodiment, the body 20 without shims 40 is initially inserted within the patient. After insertion, one or more shims 40 are inserted in the appropriate cuts 30 to adjust the stiffness as necessary. In another embodiment, the shims 40 are inserted into the body 20 prior to insertion into the patient. After insertion, additional shims 40 may be added as necessary.

Figure 14:
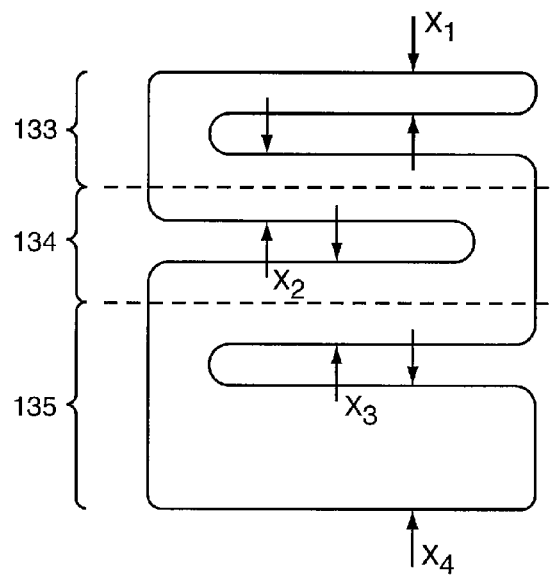
FIG. 14 is a schematic view of a body according to one embodiment.

In one embodiment as illustrated in FIG. 14, adjustment of the overall flexibility may depend upon the area that is shimmed. Body 20 may be divided into different areas that include different thicknesses X1, X2, X3, X4. The thicknesses of the areas and the size of the cuts form different sections within the body 20 each with a different spring rate. Using the embodiment of FIG. 14, a first section 133 includes a first spring rate, section 134 includes a second spring rate, and section 135 includes a third spring rate. Placing one or more shims 40 within the cuts within the specific sections affects the overall flexibility of the body 20. The surgeon is able to selectively adjust the overall flexibility depending upon which section is shimmed. Additionally, combinations of two sections may each be shimmed for further stiffness adjustment.

The implant 10 is further adaptable for insertion into the patient. The cuts 30 allow the body 20 to compress to reduce the height for insertion into spaces of different sizes. Once the body 20 is inserted, shims 40 may be inserted into the non-compressed shims 40 to provide a final stiffness to the implant 10. In one embodiment, this feature compensates for an imperfect bone preparation. The vertebral members 100 are prepared in a standard fashion. If there is a mismatch between the prepared space and the body 20, the body 20 can be compressed to fit within the prepared space as necessary.

Figure 13:
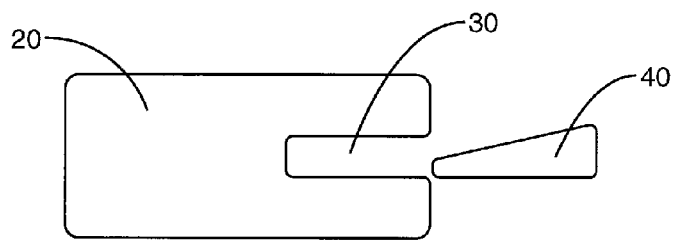
FIG. 13 is a schematic view of a body and a shim according to one embodiment.

Body 20 may deflect upon insertion into the patient resulting in the body having a smaller height. One or more of the shims 40 may be inserted into the body to expand the height to the desired amount. In one embodiment as illustrated in FIG. 13, shim 40 includes a shape to facilitate insertion into the cut 40 and increasing the height. In this embodiment, shim 40 includes a wedge shape with an angled upper surface. Increasing insertion into the body 20 results in an increase in height. The amount of increase may depend upon the specific context. In one embodiment, the height is re-established at the pre-insertion height. In another embodiment, the height is increased to an amount above the pre-insertion height. In some embodiments, the shim 40 does not fully fit within the cut 30 resulting in a portion of the shim 40 extending outward from the body 20. The surgeon may cut the shim 40 to remove the extending portion.

In one embodiment, the implant 10 is available as a kit that includes a body 20 and a number of different shims 40. A single kit may be used to construct an implant 10 with a variety of different stiffnesses depending upon the desired need. The surgeon may construct the implant 10 as necessary for the specific need. Therefore, a single kit may accommodate a variety of different surgical needs. In one embodiment, each shim 40 is designed to fit within a specific cut 30 within the body 20. In another embodiment, one or more of the shims 40 are shaped and sized to fit within multiple cuts 30.

The implant 10 may be used as a motion-preserving device that maintains motion of the vertebral members 100. In this context, the implant 10 dynamically stabilizes the vertebral members 100 and allows for continued vertebral movement. The implant 10 may also be used as a fusion device that fuses together the vertebral members 100. In some embodiments, the implant 10 functions as both a dynamic motion-preserving device and a fusion device.

The implant 10 allows the surgeon to adjust the stiffness of the body 20 depending upon the specific requirements of the patient. By way of example, a patient with osteoporosis may require a more flexible body 20 for effective fusion, while another patient may require a more rigid body 20. The implant 10 allows the surgeon to specifically adjust the stiffness of the body 20 depending upon the needs of the patient.

The implant 10 may also provide for adjustments to the stiffness during subsequent surgeries. The implant 10 may originally be introduced into the patient with a first stiffness. During a subsequent procedure, one or more shims 40 may be removed or inserted into the body 20 as necessary to adjust the stiffness to a new amount.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant for spacing apart vertebral members comprising:
 a body including an exterior surface and an interior region, the exterior surface including opposing contact surfaces configured to contact against the vertebral members when the body is inserted into a patient;
 a relief cut contained within the body and extending from the exterior surface inward to a terminal end that is disposed between the opposing contact surfaces; the relief cut having a superior side and an inferior side connected by the terminal end;
 first and second shims positioned in the relief cut and each slidably engaged with the relief cut;
 a stiffness of the implant being adjustable from a first stiffness with the relief cut being empty, a second stiffness with the first shim positioned in the relief cut, and a third stiffness with both the first and second shims positioned in the relief cut;
 a height of the implant with the first and second shims positioned in the relief cut is not greater than a distance between the opposing contact surfaces;
 wherein the relief cut is sized to simultaneously receive both the first and second shims;
 wherein, if the first and second shims are removed from the relief cut, the superior and inferior sides of the relief cut directly face each other.

2. The implant of claim 1, wherein the body is sized to fit within the intervertebral space and the exterior surface is shaped to contact the vertebral members.

3. The implant of claim 1, wherein the body is shaped to fit within an interspinous space and contact spinous processes of the vertebral members.

4. The implant of claim 1, further comprising an aperture that extends through the interior region of the body between inferior and superior sides.

5. The implant of claim 1 wherein the first and second shims have different stiffnesses.

6. The implant of claim 1, further comprising locking means for securing the first and second shims within the body.

7. The implant of claim 1, wherein at least one of the first and second shims extend outward from body when the shims are positioned in the relief cut.

8. The implant of claim 1, wherein the relief cut extends completely through the body.

9. The implant of claim 1, wherein the body and at least one of the first and second shims are constructed of different materials.

10. The implant of claim 1, wherein at least one of the shims is constructed of a resorbable material.

11. An implant for spacing apart vertebral members comprising:
a body including an exterior surface and an interior region and a central axis; the body also including a superior face and an inferior face; the central axis extending from the superior face to the inferior face;
first and second relief cuts each contained within the body and extending from the exterior surface inward into the interior region in different directions; wherein the first and second relief cuts are positioned within the interior region of the body between the superior and inferior faces of the body; wherein the first and second relief cuts overlap when viewed along the central axis;
a pair of shims, each shim being discrete from the body and including at least one surface for slidably engaging a side of one of the relief cuts to enable sliding the shim from outside the body to a position in the relief cut;
wherein insertion of one of the shims into the first relief cut causes a first stiffness in the implant that affects a first type of vertebral motion, insertion of the pair of shims into the first relief cut causes a greater second stiffness in the implant that affects the first type of vertebral motion, and insertion of one of the shims into the second relief cut causes a stiffness in the implant that affects a second type of vertebral motion;
the first relief cut having superior and inferior sides connected by a terminal end;
wherein, if the shims are removed from the first relief cut, the superior and inferior sides of the first relief cut directly face each other.

12. The implant of claim 11, wherein the first and second relief cuts extend into the interior region of the body in substantially opposing directions.

13. The implant of claim 11, wherein the first and second relief cuts include different shapes.

14. The implant of claim 11, wherein the first and second relief cuts include a substantially common shape.

15. The implant of claim 11, wherein each of the first and second relief cuts include inferior and superior sides formed by the interior region of the body.

16. The implant of claim 11, further including a first locking means for locking the shim in the first relief cut, and a second locking means for locking the shim in the second relief cut.

17. The implant of claim 11, wherein the shim is constructed of a resorbable material.

18. An implant for spacing apart vertebral members comprising:
a body including an exterior surface and an interior region; the body further comprising a central bore extending along a central axis from a superior surface of the body to an inferior surface of the body;
a plurality of relief cuts contained within the body, each extending from the exterior surface inward into the interior region and having a superior side and an inferior side connected by a terminal end; at least a first one of the plurality of relief cuts extending into the interior region from a first side of the body; at least a second one of the plurality of relief cuts extending into the interior region from an opposite second side of the body; wherein the first and second of the plurality of relief cuts are disposed in an overlapping arrangement between inferior and superior sides of the body when viewed along the central axis;
a plurality of shims discrete from the body, each including a defined shape and sized to be positioned in one of the plurality of relief cuts; at least one of the shims including a side for being slidably engaged with the wall of the first one of the relief cuts;
a stiffness of the implant being adjustable from a minimum stiffness with each of the plurality of relief cuts being empty, to a first intermediate stiffness with one of the plurality of relief cuts containing one of the plurality of shims and another of the plurality of relief cuts being empty, to a second intermediate stiffness with one of the plurality of relief cuts containing at least two of the plurality of shims and another of the plurality of relief cuts being empty, to a maximum stiffness with each of the plurality of relief cuts containing at least one of the plurality of shims;
a height of the implant when one of the plurality of shims is positioned in one of the plurality of relief cuts is not greater than a height of the body;
wherein, if the shims are removed from one of the plurality of relief cuts, the superior and inferior sides of the relief cut directly face each other.

19. The implant of claim 18 wherein the plurality of relief cuts result in a first section of the body having a first spring rate, and a second section of the body having a second spring rate.

* * * * *